United States Patent [19]

Kuwano et al.

[11] Patent Number: 4,485,305
[45] Date of Patent: Nov. 27, 1984

[54] INFRARED DETECTOR WITH VIBRATING CHOPPER

[75] Inventors: Yukinori Kuwano; Shoichi Nakano; Toshiaki Yokoo; Kenichi Shibata, all of Osaka, Japan

[73] Assignee: Sanyo Electric Co., Ltd., Osaka, Japan

[21] Appl. No.: 407,582

[22] Filed: Aug. 12, 1982

[30] Foreign Application Priority Data

Aug. 20, 1981 [JP] Japan ............................. 56-130959
Oct. 6, 1981 [JP] Japan ............................. 56-159642
Oct. 27, 1981 [JP] Japan ............................. 56-172214
Jan. 27, 1982 [JP] Japan ............................. 57-12432
Jan. 29, 1982 [JP] Japan ............................. 57-13892

[51] Int. Cl.$^3$ .............................................. G01J 5/08
[52] U.S. Cl. ................................. 250/338; 250/342; 250/351
[58] Field of Search ............. 250/338 PY, 338, 342, 250/347, 349, 350, 351; 356/25, 26

[56] References Cited

U.S. PATENT DOCUMENTS 3,175,092 3/1965 Leftwich ........................... 250/233
3,925,668 12/1975 Anderson et al. ................. 250/351

OTHER PUBLICATIONS

Gary Frodsham, "Operation of Tuned Fork Light Choppers at Liquid Helium Temperatures", *Rev. Sci. Instrum.*, vol. 46, No. 3, (Mar. 1975), pp. 312–316.

Primary Examiner—Janice A. Howell
Assistant Examiner—Constantine Hannaher
Attorney, Agent, or Firm—Darby & Darby

[57] ABSTRACT

An infrared ray detector comprising an infrared ray detecting body, a pair of opposing portions, a bimorph vibrator connected to the pair of opposing portions for intermitting infrared rays incident upon the detector, and a housing containing these elements, the housing being provided with an opening for incidence of infrared rays. The pair of opposing portions comprise infrared ray transmitting portions and infrared ray non-transmitting portions. The infrared ray transmitting portions in one of opposing portions is periodically overlapped by the bimorph vibrator with the infrared ray transmitting portions or infrared ray non-transmitting portions in the other opposing portion, so that incident infrared rays are intermitted.

37 Claims, 29 Drawing Figures (a)

(b)

INFRARED DETECTOR WITH VIBRATING CHOPPER

BACKGROUND OF THE INVENTION

1. Field of the Invention

The present invention relates to an infrared ray detector, and more particularly, an infrared ray detector including intermitting means for intermitting an incident infrared ray. An infrared ray detector for detecting existence, temperature and the like of substance by the infrared ray radiated by the substance have been widely put into practice. However, for example, in an infrared ray detector such as a pyroelectric type infrared ray detector for generating electric charges responsive to change of an amount of an incident infrared ray, it is necessary to intermit periodically an incident infrared ray in order to ensure a precise measurement. The present invention relates to an infrared ray detector including such means for intermitting these infrared rays.

2. Description of the Prior Art

Conventionally, as means for intermitting infrared rays incident upon an infrared ray detector, an apparatus such as shown in FIGS. 1A and 1B has been used. The apparatus is disposed in front of an infrared ray detector 1 and comprises a motor 2 and a metal plate chopper 3 rotatably driven in a periodical manner by the motor 2. However, the apparatus as shown in FIGS. 1A and 1B requires a relatively large chopper 3 which prevent the apparatus from being small-sized. Furthermore, since the motor 2 sometimes irregularly rotates, the chopper 3 cannot be precisely and periodically rotated and thus there was a drawback that the precision for detection is relatively low.

In order to solve the above described problems, a structure for intermitting an incident infrared ray using a shutter body connected to a piezoelectric vibrator is disclosed in the Japanese Patent laying open Nos. 54418/1980 and 54419/1980 which are laid open for public inspection on Apr. 21, 1980, respectively. However, since the whole shutter body moves across the path of the infrared ray, the amount of movement of the shutter body must be made large and thus it is necessary to use a relatively large piezoelectric vibrator. As a result, it can be hardly said that such structure contributes to a miniaturization of an infrared ray detector.

On the other hand, the present inventors disclosed in the Japanese laying open No. 160628/1981 laid open for public inspection on Dec. 10, 1981, the structure in which a pair of opposing portions vibrated by a piezoelectric vibrator, which comprises infrared ray transmitting portions and infrared ray non-transmitting portions, are disposed in front of a window for incidence of an infrared ray in an infrared ray detector. However, in this prior art, besides an infrared ray detector, it is necessary to include an additional structure having a piezoelectric vibrator and the like and thus just as each prior art as described in the foregoing, it does not contribute to a miniaturization of an infrared ray detector per se.

SUMMARY OF THE INVENTION

Briefly stated, the present invention is directed to an infrared ray detector comprising an infrared ray detecting body, a pair of opposing portions having a plurality of infrared ray non-transmitting portions and infrared ray transmitting portions, intermitting means for intermitting incident infrared rays through the pair of opposing portions, and a housing containing the infrared ray detecting body, the pair of opposing portions and the intermitting means, and the housing having an opening for incidence of infrared rays. The infrared ray detecting body comprises various kinds of infrared ray detecting bodies such as a phototransistor, as well as a pyroelectric type infrared ray detecting body. Preferably, a piezoelectric vibrator can be used as intermitting means. Furthermore, as a filter for transmitting an incident infrared ray, a narrow band infrared ray filter for transmitting only an infrared ray of a band which the substance to be detected absorbs may be provided in the vicinity of an opening of the housing. In addition to the filter transmitting infrared rays of all bands, which is provided in the opening, a narrow band filter may be provided.

The intermitting means is of a type moving only one opposing portion of the pair of opposing portions or is of a structure such that a pair of moving means move both of the opposing portions, respectively. Preferably, it may be structured such that an infrared ray detecting body comprises a plurality of detecting portions and a plurality of infrared ray transmitting filters are disposed opposing to a plurality of detecting portions, respectively, which have absorbing bands different from each other. Preferably, the plurality of filters comprise a filter or filters for fire prevention and a filter or filters for detecting a human body, respectively.

A plurality of detecting portions are connected in such a manner that the directions of polarization are opposite to each other for each pair, so that it becomes possible to cancel a noise.

Accordingly, a principal object of the present invention is to provide a small-sized and light infrared ray detector which can overcome the above described problems.

Another object of the present invention is to provide an infrared ray detector with an excellent detecting precision.

These objects and other objects, features, aspects and advantages of the present invention will become more apparent from the following detailed description of the present invention when taken in conjunction with the accompanying drawings.

DETAILED DESCRIPTION OF THE PREFERRED EMBODIMENT

Figure 1A:
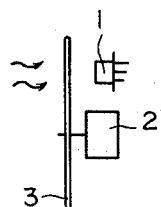
FIGS 1A and 1B are a side view and a plane view, respectively, showing a conventional infrared ray detecting apparatus including a conventional infrared ray intermitting means.
Figure 1B:
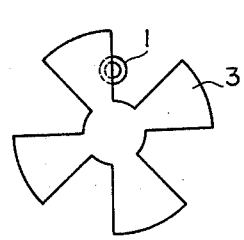
Figure 2:
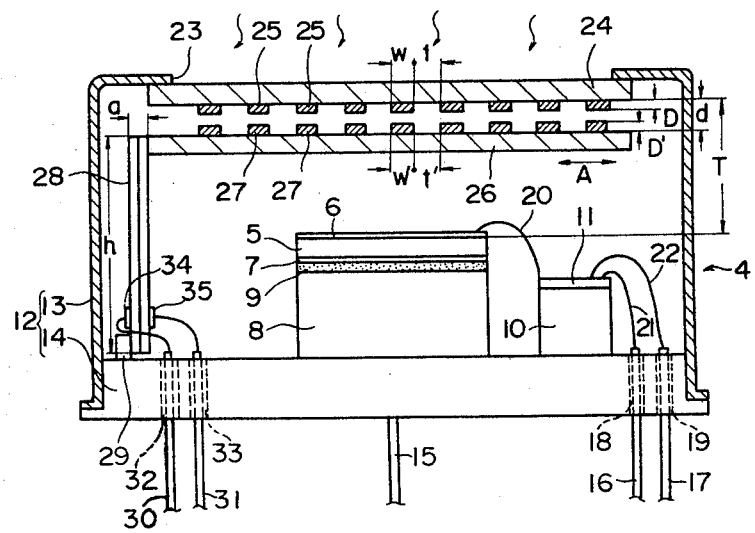
FIG. 2 is a side sectional view showing an embodiment of the present invention, wherein one opposing portion, that is, an opposing portion near an infrared ray detecting body, is connected to a piezoelectric vibrator.

FIG. 2 is a side sectional view of an infrared ray detector of the first embodiment of the present invention. An infrared ray detector 4 comprises an infrared ray detecting body or element 5 comprised of single crystal of lithium tantalate ($LiTaO_3$) and generating electric charges responsive to an amount of change of incident infrared rays. In a front surface and a back surface of the infrared ray detecting body 5 a front surface electrode 6 and a back surface electrode 7 are formed by means of Nichrome evaporation film. The infrared ray detecting body 5 is fixed on a supporting bed 8 made of metal such as copper, phosphor bronze and the like by a conductive adhesive 9 such as silver paste and the like in such a direction that the back surface electrode 7 is opposed to an upper surface of the supporting bed 8.

An impedance converter circuit 11 is disposed on an alumina substrate 10. The impedance converter circuit 11 is a circuit for converting an output impedance of the infrared ray detecting body 5 into a low resistance because of a high resistance value of the infrared ray detecting body 5 per se. The above described supporting bed 8 and alumina substrate 10 are fixed on a header 14 within a housing 12 which is structured by a cap 13 and the header 14 made of metal. A ground terminal 15 is directly embedded in the header 14 and is electrically connected to the above described back surface electrode 7 through the supporting bed 8 and the conductive adhesive 9. In addition, a first lead terminal 16 and a second lead terminal 17 are embedded in the header 14 while being insulated from each other by insulating materials 18 and 19. The front surface electrode 6 of the infrared ray detecting body 5 and the impedance converting circuit 11 are connected to each other by a lead wire 20 and the impedance converter circuit 11 and the first and second lead terminals 16 and 17 are connected by lead wires 21 and 22, respectively.

In the cap 13, an opening 23 is formed as a window for entering an infrared rays from the side of the front surface electrode 6 to the infrared ray detecting body 5. The opening 23 may be a circular shape of 8 mm in diameter, a square shape of 8 mm square or a rectangular shape. A first infrared ray transmitting portion 24 is adhered to the cap 13 so as to close the opening 23 thereof. The first infrared ray transmitting portion 24 is structured by a silicon or germanium plate of several hundred microns in thickness, which transmission rate to the infrared ray of 2-15 $\mu$m in wavelength is high. It should be pointed out that a distance T between the first infrared ray transmitting portion 24 and the infrared ray detecting body 5 is in range of 500 $\mu$m ~ 3 cm.

A plurality of stripes of the first infrared ray non-transmitting portions 25 are provided in a lower surface of the first infrared ray transmitting portion 24 in a direction perpendicular to the surface of the drawing. The first infrared ray non-transmitting portions 25 are structured by metal such as aluminum, gold, silver and the like, the width W thereof being 1 $\mu$m ~ 2 mm, and the thickness D being 0.1 ~ 100 $\mu$m. The infrared ray non-transmitting portions 25, 25 are spaced apart from a predetermined spacing t which is the same as the above described width W.

A second infrared ray transmitting portion 26 is provided within the housing 12 so as to be opposed to the above described first infrared ray transmitting portion 24 with a distance d (0.1 μm ~ 1 cm). The second infrared ray transmitting portion 26 has the same shape as the opening 23, just as the first infrared ray transmitting portion 24, and is structured by a silicon or germanium plate of several hundred microns in thickness, which transmission rate to the infrared ray of 2-15 μm in wave length is high. A plurality of stripes of second infrared ray non-transmitting portions 27, 27 are provided in an upper surface of the second infrared ray transmitting portion 26 in the same direction of the first infrared ray non-transmitting portions 25, 25, that is, in a direction perpendicular to the surface of the drawing. The second infrared ray non-transmitting portions 27, 27 are made of infrared ray non-transmitting material such as aluminum, gold, silver and the like, just as the first infrared ray non-transmitting portions 25, 25, the width W' of the second infrared ray non-transmitting portions 27, 27 being 1 μm ~ 2 mm and the thickness D' being 0.1 ~ 100 μm. In addition, the second infrared ray non-transmitting portions 27, 27 are spaced from each other with a predetermined distance t' which is the same as the width W'. As described in the foregoing, a pair of opposing portions are structured by one opposing portion comprised of the first infrared ray non-transmitting portions 25 and infrared ray transmitting spaces between the first infrared ray non-transmitting portions 25, and the other opposing portion comprised of the second infrared ray non-transmitting portion 27 and infrared ray transmitting spaces between the second infrared ray non-transmitting portions 27, and are contained within the housing 12.

A vibrator formed by sticking two piezoelectric plates, that is, a bimorph vibrator 28, has a lower end thereof fixed to an insulating bed 29 provided in the header 14, the second infrared ray transmitting portion 26 being fixed to an upper portion of the bimorph vibrator 28. The bimorph vibrator 28 is a rectangular parallelpiped, the height h being 1-30 mm, the thickness a being 50 μm-5 mm and the width (the size in a direction perpendicular to the surface of the drawing) being 0.5-15 mm. The bimorph vibrator 28 may be formed of single crystals such as rock crystal, Rochelle salt, ethylenediamine tartrate, potassium tartrate, potassium phosphate, ammonium phosphate, lithium sulfate, barium titanate, glycine sulfate and the like, and ceramic materials such as ceramic containing barium titanate, ceramic containing lead zirconate titanate, ceramic containing niobate and the like.

The third and fourth lead terminals 30 and 31 are inserted into the header 14 through insulating materials 32 and 33 and are connected to electrodes 34 and 35, respectively, provided on both surfaces of the bimorph vibrator 28.

In the infrared ray detector 4 of the first embodiment of the present invention structured in the foregoing, if and when an alternate current signal with a predetermined amplitude is applied between the electrodes 34 and 35 through the third and fourth lead lines 30 and 31, the bimorph vibrator 28 make a flexure according to frequency of the alternate current signal to vibrate periodically the second infrared ray transmitting element 26 in a direction of an arrow A. As a result, the second infrared ray non-transmitting portions 27, 27 are periodically overlapped with the first infrared ray non-transmitting elements 25, 25 or with infrared ray transmitting portions between the first infrared ray non-transmitting portions 25, 25. At that time, infrared rays from an object to be detected provided outside the infrared ray detector 4 periodically enter into the infrared ray detecting body 5. More particularly, infrared rays incident upon the infrared ray detecting body 5 periodically change and thus the infrared ray detecting body 5 generates electrical charges according to an amount of the change. The charges are based upon the difference in temperature between a temperature of the object to be detected and a room temperature.

Figure 3:
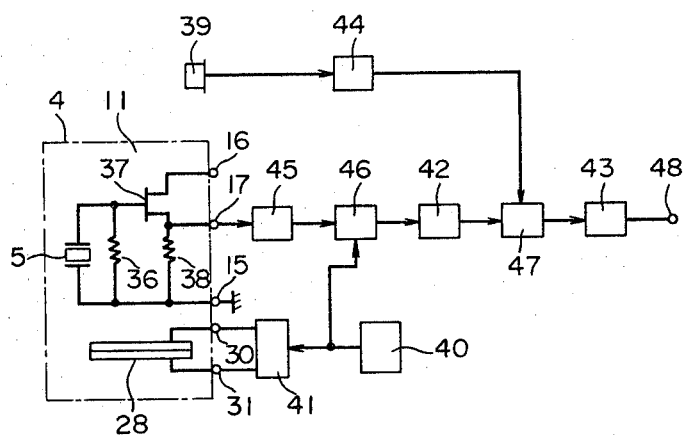
FIG. 3 is a circuit including an infrared ray detector of the first embodiment as shown in FIG. 2.

FIG. 3 shows a circuit including an infrared ray detector 4 of the present invention as shown in FIG. 2, wherein the impedance converter circuit 11 within the infrared ray detector 4 is structured by a high input resistor 36 of $10^{10} \sim 10^{11} \Omega$, a field effect transistor (FET) 37 and an output resistor 38 of approximate 10KΩ. The infrared ray detector 4 is supplied with a direct voltage from the first lead terminal 16 and an alternate current signal is outputted from the second lead terminal 17 according to the difference in temperature between a temperature of the object to be detected and a room temperature. Measurement of a room temperature is made by a diode 39 and the bimorph vibrator 28 is periodically vibrated by an oscillator 40 comprised of an astable multivibrator and a driver circuit 41 for outputting alternate current signal based on periodical pulses from the oscillator 40. 42, 43 and 44 denote direct current amplifiers, 45 denotes a filter amplifier, and 46 denotes a synchronizing rectifier. This synchronizing rectifier 46 synchronizes an alternating current signal from the infrared ray detector 4 with pulses from the oscillator 40 and outputs a positive direct current signal according to the temperature difference in case where the temperature of the object to be detected is higher than a room temperature and a negative direct current signal according to the temperature difference in case where the temperature of the object to be detected is lower than a room temperature. The output from the synchronizing rectifier 46 and the output from the diode 39 are synthesized in a synthesizing circuit 47 which outputs a signal according to the temperature of the object to be detected. 48 is an output terminal for outputting such a temperature to a desired circuit.

It should be pointed out that the circuit of FIG. 3 structured and operated as described in the foregoing can apply to all of the embodiments described subsequently.

Figure 4:
FIG. 4 is a drawing showing a shape of an output signal from the circuit as shown in FIG. 3.

FIG. 4 shows a wave shape of an output signal from the infrared ray detector of the first embodiment. In the infrared ray detector 4 in this embodiment, the second infrared ray non-transmitting portions 27 and infrared ray transmitting spaces between the second infrared ray non-transmitting portions, which structure one opposing portion of a pair of opposing portions, are vibrated by a piezoelectric vibrator 28 and thus an output signal withdrawn from the second lead terminal 17 becomes an intermittent wave shape as shown in FIG. 4. Accordingly, as compared with a wave shape of an output signal (shown in dotted line in FIG. 4) in case where a pair of opposing portions do not exist, an output wave shape from the infrared ray detector 4 indicates a sharp level change. As a result, a circuit of a subsequent stage to which an output is applied, for example, a differential circuit and the like, can precisely detect the level change.

Figure 5:
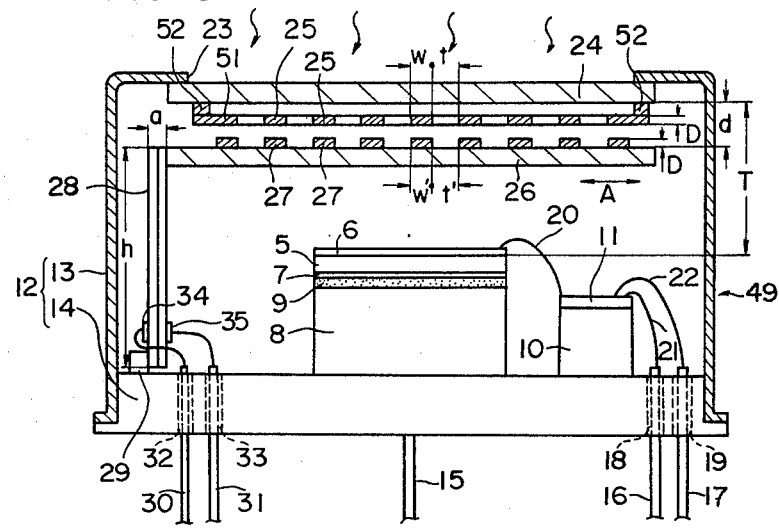
FIG. 5 shows a side sectional view of the infrared ray detector of the second embodiment of the present invention, wherein the other opposing portion is connected to an infrared ray transmitting filter.

FIG. 5 is a side sectional view of an infrared ray detector 49 of the second embodiment of the present invention. In this embodiment, an infrared ray detector 49 is adapted such that a frame 51 which is integrally provided with the first infrared ray non-transmitting portions 25, 25 is disposed on the first infrared ray transmitting portion 24 through spacers 52, 52. Since other points are the same as the first embodiment described in the foregoing, the detailed description will be omitted.

Figure 6:
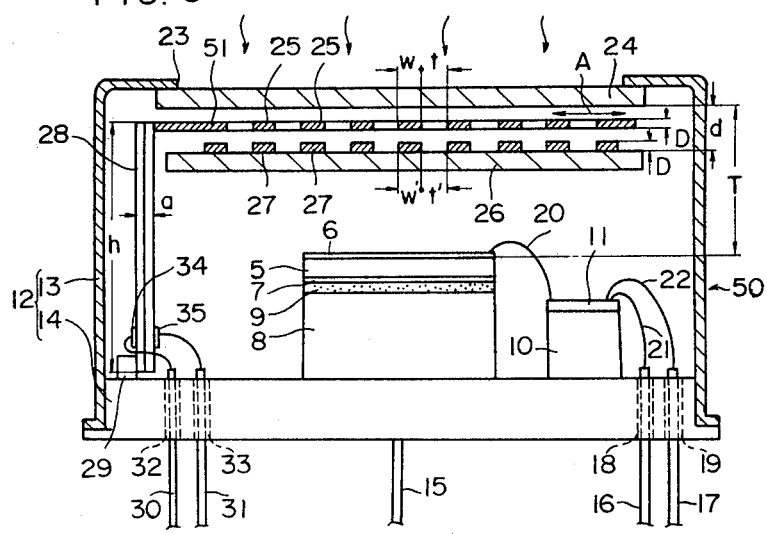
FIG. 6 is a side sectional view of an infrared ray detector of the third embodiment of the present invention, wherein the other opposing portion of a frame-like shape is connected to a piezoelectric vibrator.

FIG. 6 is a side sectional view showing an infrared ray detector 50 of the third embodiment of the present invention. In the infrared ray detector 50 of the embodiment, the second infrared ray transmitting portion 26 is fixed to other fixing bed (not shown) provided in the housing 12 and a frame 51 is fixed to a bimorph vibrator 28. The other points are the same as the first embodiment and thus the detailed description thereof will be omitted.

Figure 7:
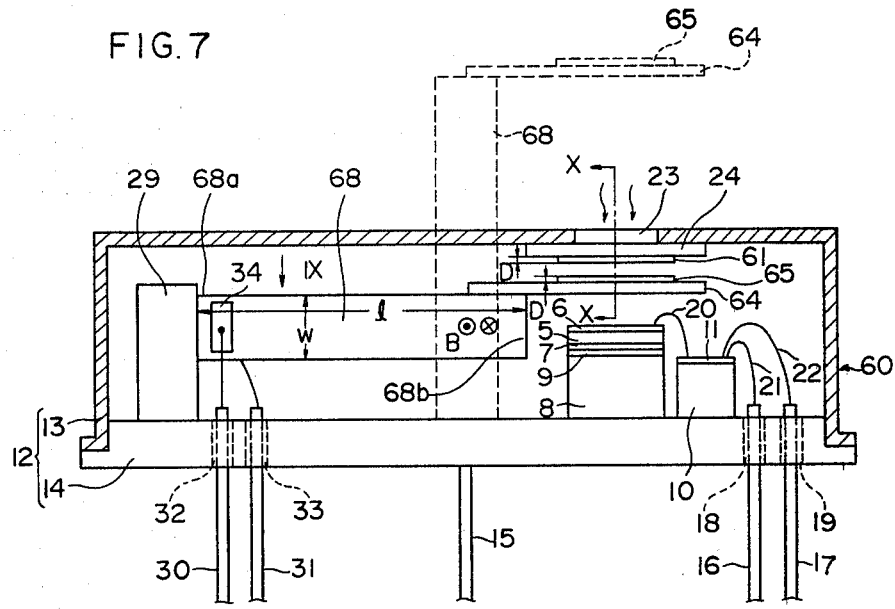
FIG. 7 is a side sectional view of an infrared ray detector of the fourth embodiment of the present invention, wherein a piezoelectric vibrator is disposed such that the longitudinal direction thereof is coincident with a direction perpendicular to an incident infrared ray.
Figure 8A:
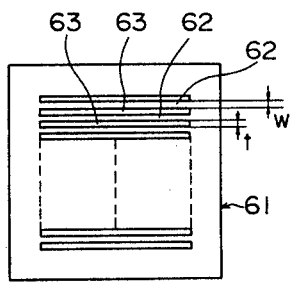
FIGS. 8A and 8B are plan views showing a pair of opposing portions having transmittable portions and non-transmittable portions of infrared rays, which are used in the infrared ray detector of the fourth embodiment of the present invention as shown in FIG. 7.
Figure 8B:
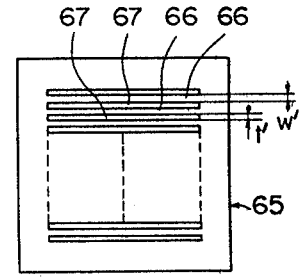

FIG. 7 is a side sectional view showing an infrared ray detector of the fourth embodiment of the present invention. In the infrared ray detector 60 of the embodiment, a planar first opposed element 61 is fixed to a lower surface of the first infrared ray transmitting portion 24 so as to be opposed to an opening 23. The first opposing portion 61 comprises a plurality of an infrared ray non-transmitting portions 62, 62 comprised of infrared ray non-transmitting materials such as aluminum, gold, silver and the like and extended in a linear manner in a direction parallel to the surface of the drawing of FIG. 8A and the first infrared ray transmitting portions 63, 63 placed between the first infrared ray non-transmitting portions 62, 62, respectively. The width W of the first infrared ray non-transmitting portions 62, 62 is 1 $\mu$m-2 mm, the thickness D is 0.1-100 $\mu$m, and the width t of the first infrared ray transmitting portions 63, 63 is the same as the width W. The second infrared ray transmitting portion 64 is disposed within a housing 12 to be adjacent and opposed to the first infrared ray transmitting portion 24. The second infrared ray transmitting portion 64 includes the same structure as the first infrared ray transmitting portion 24. To the upper surface of the second infrared ray transmitting element 64 is fixed the second opposing portion 65 to be opposed to the first opposing portion 61. As shown in FIG. 8B, the second opposing portion 65 comprises a plurality of the second infrared ray non-transmitting portions 66, 66 comprised of the same material as the first infrared ray non-transmitting portion 62 and extended in a linear manner to a direction parallel to the surface of the drawing, and the second infrared ray transmitting portions 67, 67 placed between the second infrared ray non-transmitting portions 66, 66, respectively.

In the infrared ray detector 60 of the embodiment as shown in FIG. 7, the bimorph vibrator 68 has a left end portion 68a fixed to an insulating bed 29 provided in the header 14, the second infrared ray transmitting portion 64 being fixed to a right end portion 68b, so that the bimorph vibrator 68 is placed to be longer in a direction perpendicular to an incident direction of infrared ray, that is, in a lateral direction. Other structure is the same as the first embodiment described in the foregoing and thus the same reference numerals are labeled and the detailed description will be omitted.

Figure 9:
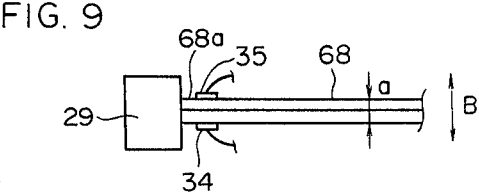
FIG. 9 is a partial plan view as viewed from an arrow IX direction in FIG. 7.
Figure 10:
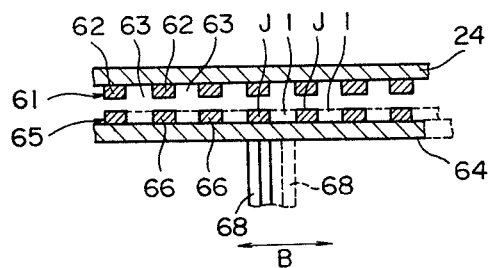
FIG. 10 is a cross sectional view taken along a line X—X of FIG. 7.

As described in the foregoing, in the FIG. 7 embodiment, the bimorph vibrator 68 makes a flexure according to a frequency of an alternating current signal and periodically vibrates the second infrared ray transmitting portion 64 in a B direction perpendicular to the surface of the drawing (see FIG. 9). In such a case, since the length l of the bimorph vibrator 68 is relatively longer as described in the foregoing, the right end portion 68b thereof largely vibrates and thus the second opposing portion 65 is also largely vibrates, as shown in FIG. 10 in detail, such that the portion 65 periodically placed in portions in which the second infrared ray non-transmitting portions 66, 66 overlap with the first infrared ray transmitting portions 63, 63 of the first opposing portion 61 (indicated by a dotted line I), and the portions in which the second infrared ray non-transmitting portions 66, 66 overlap with the first infrared ray non-transmitting portions 62, 62 (indicated by a solid line J). At that time, the second opposing portion 65 is usually held in a state parallel to the first opposing portion 61.

Figure 11:
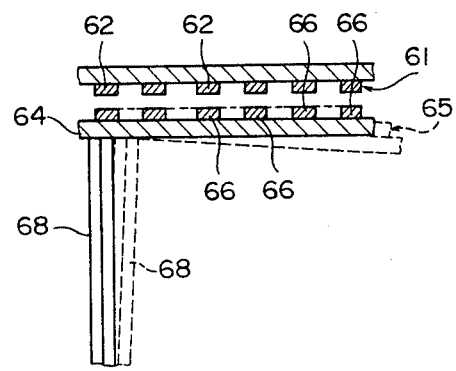
FIG. 11 shows a cross sectional view of an infrared ray detector as a comparable example, corresponding to FIG. 10.

As shown in a dotted line in FIG. 7, if and when the bimorph vibrator 68 is disposed to be longer in an incident direction of infrared ray, the infrared ray detector per se must necessarily become larger in an incident direction of infrared ray and thus it is difficult to fit the infrared ray detector in case where the size in an incident direction of infrared ray in a space for fitting the infrared ray detector is small. In such a case, the second opposing portion 65 vibrates, as shown in FIG. 11, so that the portion 65 is placed in the position not parallel to the first opposing portion 61.

However, in the infrared ray detector 60 in this embodiment, the bimorph vibrator 68 is placed to be longer in a lateral direction so as to vibrate while keeping the second opposing portion 65 parallel to the first opposing portion 61, and is placed so as to vibrate in a B direction so that the size in an incident direction of infrared ray can be made small.

Figure 12:
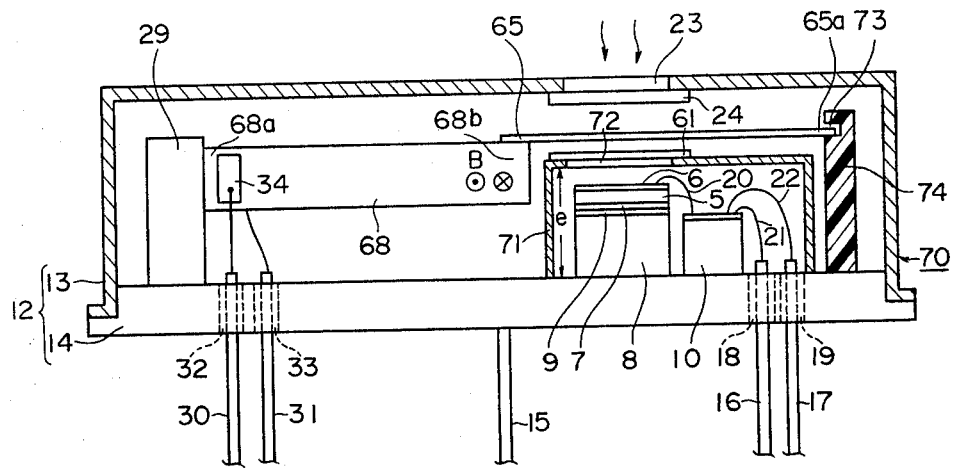
FIG. 12 is a side sectional view of an infrared ray detector of the fifth embodiment of the present invention.

FIG. 12 is a side sectional view showing an infrared ray detector 70 of the fifth embodiment of the present invention. In the infrared ray detector 70 in this embodiment, a shield member 71 of approximate 5 mm in height for covering the infrared ray detecting element 5 and an impedance converter circuit 11 is provided, the shield member 71 being made of metal material such as aluminum and the like and being formed with an opening 72 in a portion placed in the upper of the detecting element 5. The first opposing portion 61 is sticked to the opening 72. The shield member 71 prevents a noise based on vibration of the bimorph vibrator 68 from being induced in the infrared ray detecting element 5 and the impedance converter circuit 11. The second opposing portion 65 is directly sticked to the right end portion 68b of the bimorph vibrator 68. A groove 73 slidably supporting a free end 65a of the second opposing portion 65 is formed in the supporting bed 74 made of a synthetic resin such as Teflon and the like. Other structure is the same as the fourth embodiment of the present invention as shown in FIG. 7 and thus the detailed description thereof will be omitted.

Figure 13:
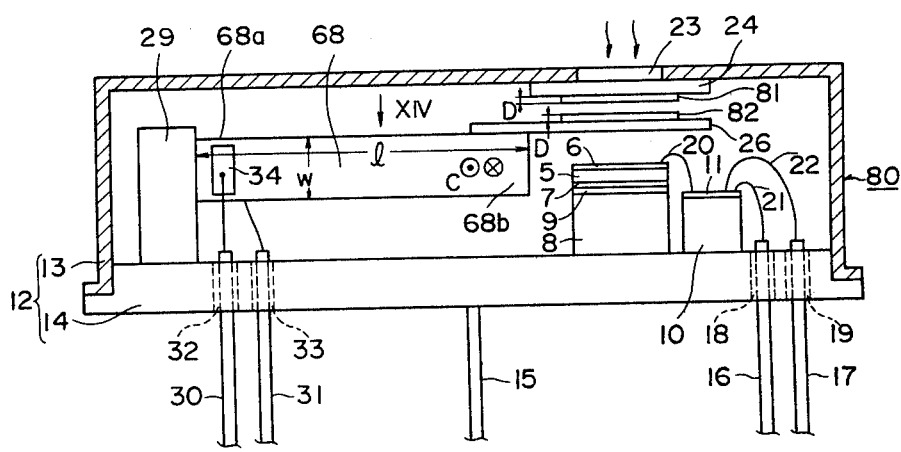
FIG. 13 is a side sectional view of the sixth embodiment of the present invention, wherein a piezoelectric vibrator is disposed such that the longitudinal direction thereof is perpendicular to an incident direction of an infrared ray.
Figure 14:
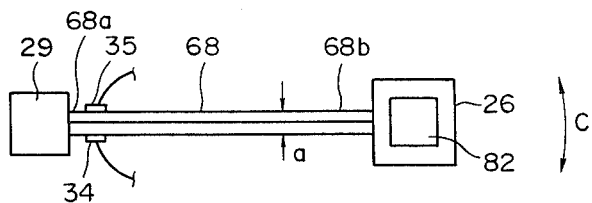
FIG. 14 is a partial plan view as viewed from an arrow X IV in FIG. 13.

FIG. 13 is a side sectional view of the sixth embodiment of the present invention. The feature of the infrared ray detector 80 of the sixth embodiment of the present invention resides in the shape and size of a pair of opposing portions, that is, the first opposing portion 81 and the second opposing portion 82. As clearly seen from FIG. 14 which is a partial plan view as viewed from an arrow XIV direction of FIG. 13, the second opposing portion 82 is vibrated in an arrow C direction by a piezoelectric vibrator 68. As clearly seen from FIG. 15B, the second opposing portion 82 comprises a plurality of the second infrared ray non-transmitting portions 83, 83 extended in a linear manner in a direction approximately parallel to the surface of the drawing (see FIG. 13), and the second infrared ray transmitting portions 84, 84 placed within the second infrared ray non-transmitting portions 83, 83, respectively and having the same shape and size as those of the second infrared ray non-transmitting portions 83, 83. The size in each portion of the second infrared ray non-transmitting portions 83, 83 and the second infrared ray transmitting portions 84, 84 is proportional to the width of vibration of each portion. Accordingly, since the second opposing portion 82 vibrates in a C direction in an arcuate manner, the second infrared ray non-transmitting portions 83, 83 and the second infrared ray transmitting portions 84, 84 form a sector such that the size of direction of vibration in a portion nearest to the bimorph vibrator 68 becomes a minimum width $W_1$ and the size of direction of vibration in a portion farthest from the bimorph 68 becomes a maximum width $W_2$.

Figure 15A:
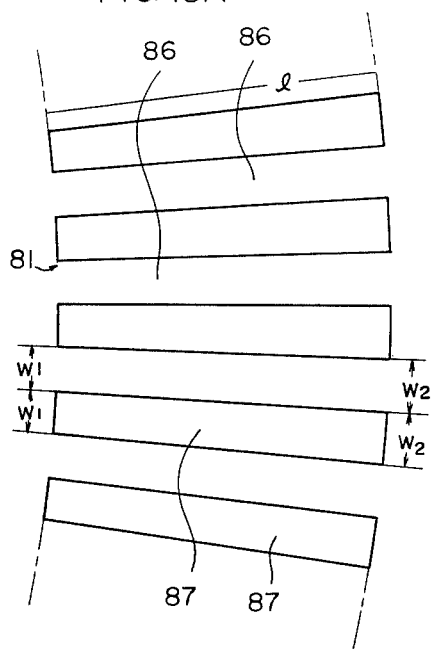
FIGS. 15A and 15B are plan views showing in an enlarged manner main portions of a pair of opposing portions used in the sixth embodiment of the present invention as shown in FIG. 13.
Figure 15B:
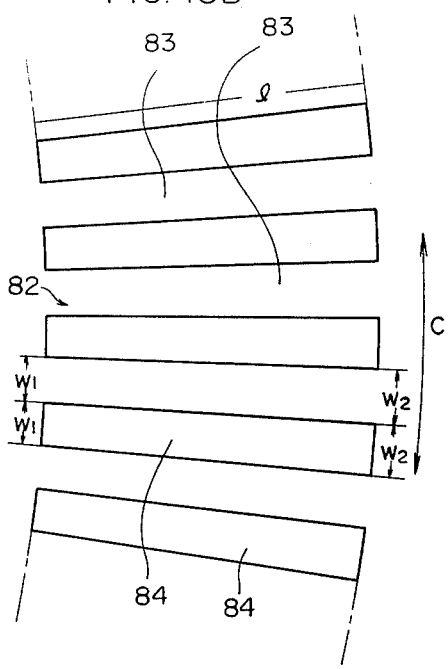

On the other hand, the first opposing portion 81 is made of the same material as the second infrared ray non-transmitting portions 83, 83 and comprises a plurality of the first infrared ray non-transmitting portions 86, 86 extended in a linear manner as shown in FIG. 15A in a direction approximately parallel to the surface of the drawing (see FIG. 13), and the first infrared ray transmitting portions 87, 87 placed between the first infrared ray non-transmitting portions, respectively. The first infrared ray non-transmitting portions 86, 86 and the first infrared ray transmitting portions 87, 87 have the same sector shape and size as those of the above described second infrared ray non-transmitting portions 83, 83 and the second infrared ray transmitting portions 84, 84 of the second opposing portion 82.

By way of one example of the specific size and shape, the above described widths $W_1$ and $W_2$ are 100 $\mu$m and 120 $\mu$m, respectively, the length l is 3 mm and the thickness D is 0.1–100 $\mu$m.

Figure 16:
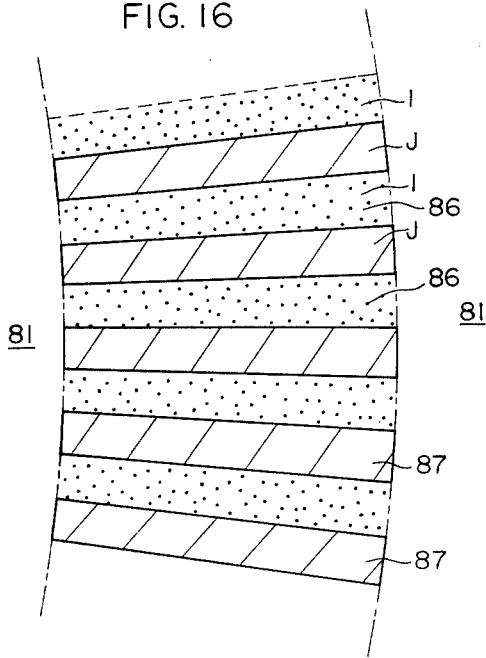
FIG. 16 is a drawing of operational states of the pair of opposing portions as shown in FIGS. 15A and 15B.
Figure 18:
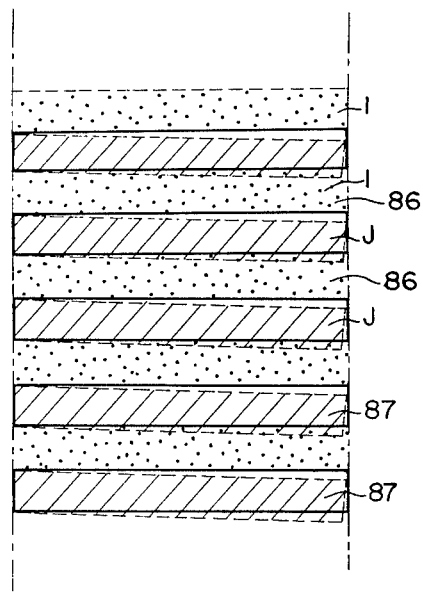
FIG. 18 is a drawing of an operational state of the pair of opposing portions as shown in FIGS. 17A and 17B.
Figure 17A:
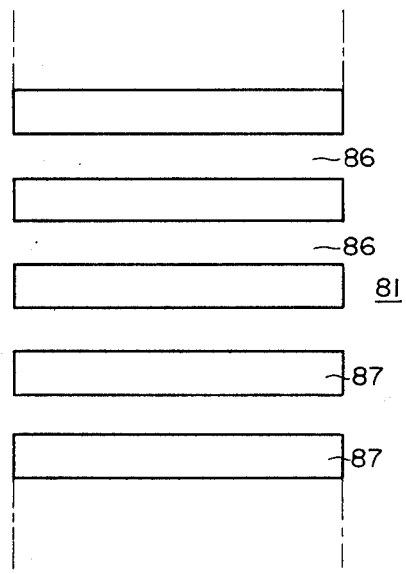
FIGS. 17A and 17B are general enlarged plan views of the infrared ray detectors corresponding to those of FIGS. 15A and 15B, respectively.
Figure 17B:
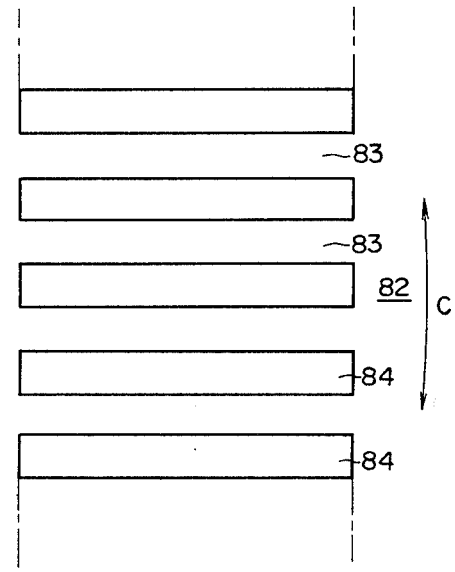

In the sixth embodiment of the present invention as structured in the foregoing, at the time of vibration of the bimorph vibrator 68, the second infrared ray non-transmitting portions 83, 83 of the second opposing portion 82 vibrate, as shown in detail in FIG. 16, such that the portions 83, 83 alternately and completely overlap with the first infrared ray non-transmitting portions 86, 86 and the first infrared ray transmitting portions 87, 87 of the first opposing portion 81, that is, the portions 83, 83 are placed in the dot areas I and oblique line areas J. In this respect, it is usual that the width of the first infrared ray non-transmitting portions 86, 86, the first infrared ray transmitting portions 87, 87, the second infrared ray non-transmitting portions 83, 83 and the second infrared ray transmitting portions 84, 84 are made constant as shown in FIGS. 17A and 17B. In such a case, since the second opposing portion 82 vibrates in a C direction in an arcuate manner, the second infrared ray non-transmitting portions 83, 83, for example, do not perfectly overlap with the first infrared ray non-transmitting portions 86, 86, as shown in FIG. 18. Accordingly, even if infrared rays from the object to be detected outside of the infrared ray detector 80 are periodically intermitted so that the infrared ray incident upon the infrared ray detecting element 5 is periodically changed, that is, is modified in a alternating manner, the degree of the modification is poor and thus the signal-noise ratio in the infrared ray detecting element 5 decreases.

In this respect, in the above described infrared ray detector 80, since the second infrared ray non-transmitting portions 83, 83 are completely overlapped with the first infrared ray non-transmitting portions 86, 86 and the first infrared ray transmitting portions 87, 87, the degree of modulation of the infrared ray incident upon the infrared ray detecting element 5 is excellent and thus the signal-noise ratio in the infrared ray detecting element 5 is drastically enhanced. The output from the infrared ray detecting element 5 depends on the difference in temperature between a temperature of the object to be detected and a room temperature.

Figure 19:
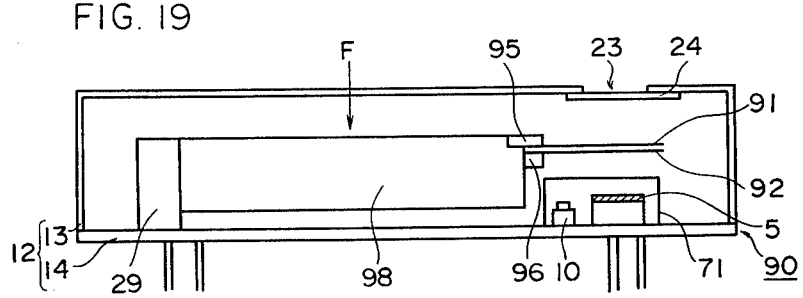
FIG. 19 is a side sectional view of the seventh embodiment of the present invention, wherein a pair of piezoelectric vibrators are connected to a pair of opposing portions, respectively.
Figure 20:
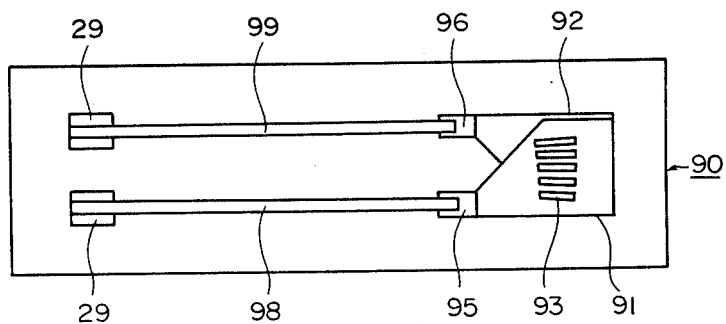
FIG. 20 is a plan view of an infrared ray detector of the seventh embodiment of the present invention as shown in FIG. 19.

FIG. 19 is a schematic side sectional view of an infrared ray detector 90 of the seventh embodiment of the present invention and FIG. 20 is a plan view as viewed from a direction of an arrow F in FIG. 19. The feature of the infrared ray detector 90 of the embodiment resides in the point that a pair of the piezoelectric vibrators 98, 99 are provided. More particularly, a pair of opposing portions 91, 92, are connected to a pair of the piezoelectric vibrators 98, 99. The pair of opposing portions 91, 92 can be structured in the same manner as each embodiment described in the foregoing. Accordingly, each of opposing portions 91, 92 comprises infrared ray transmitting portions and infrared ray non-transmitting portions. The respective opposing portions 91, 92 are overlapped with respect to each other such that each opposing portion periodically intermits infrared rays by vibrations of the piezoelectric vibrators 98, 99 connected to the opposing portions 91, 92 through supports 95, 96 made of synthetic resin, respectively. It is pointed out that although the shape of infrared ray transmitting portion of each of the opposing portions 91, 92 may be formed just as a slit 93 having a predetermined width, as shown in FIG. 20, it may have any shape as long as the shape may be such that slits provided in both of the opposing portions 91, 92 can be periodically overlapped with respect to each other. It should be further pointed out that the structure for vibrating both of opposing portions by a pair of piezoelectric vibrators can apply to all of the embodiments disclosed in this specification.

Figure 21:
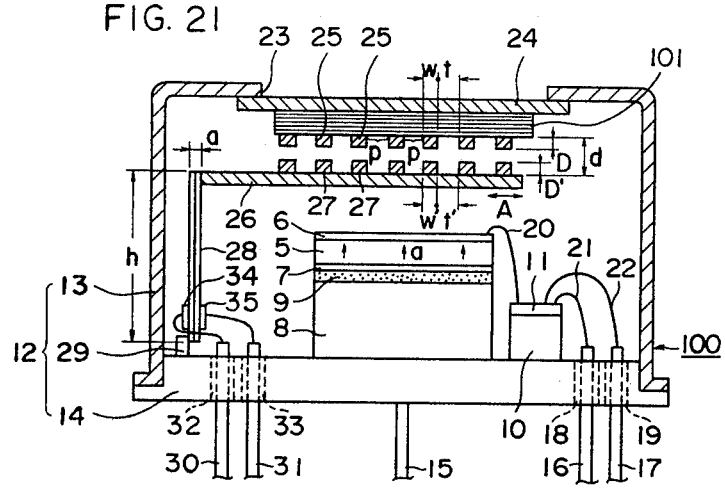
FIG. 21 is a side sectional view of an infrared ray detector of the eighth embodiment of the present invention, wherein a gas filter is provided in addition to an infrared ray transmitting filter fixed to a window for incidence of infrared ray.

FIG. 21 is a side sectional view of an infrared ray detector of the eighth embodiment of the present invention. The infrared ray detector 100 of this embodiment is of a type used for detecting various gases such as methane, carbon oxide, nitrogen oxide and nitrogen dioxide. The infrared ray detector 100, that is, gas sensor 100 is basically an improvement of the structure of the first embodiment of the present invention, that is, the embodiment as shown in FIG. 2. The feature of this embodiment resides in the point that a gas filter 101 is provided between the first infrared ray transmitting portion 24 and the first infrared ray non-transmitting portion 25. Accordingly, the infrared rays through the first infrared ray transmitting portion 24 can be applied to the infrared ray detecting element 5 through the filter 101 and the pair of opposing portions. The gas filter 101 is a narrow band infrared ray filter which substantially transmits only an infrared ray absorbed by the gas to be detected and is comprised of a multilayer structure of a substance of high index of reflexion such as lead telluride (PbTe) and of a substance of low index of reflexion such as zinc sulfide (ZnS). In case where the gases to be detected are methane ($CH_4$), carbon oxide (CO), nitrogen oxide (NO) or nitrogen dioxide ($NO_2$), the wavelength of infrared rays absorbed by $CH_4$, CO, NO, $NO_2$ are 3.3, 4.7, 5.3, and 6.2 $\mu$m, respectively and thus the neighborhood of the wavelength 3.3, 4.7, 5.3, 6.2, $\mu$m are selected as transmitting infrared ray regions of narrow band infrared ray filter 101.

If and when gas leakage is not caused, the gas sensor having the above described structure operates as described in the following. First, it is assumed that no leakage of $CH_4$, $CO$, $NO$ or $NO_2$ is caused. In case where, in such a state, said second infrared ray non-transmitting portions 27, 27 are overlapped with a P portion in the narrow band infrared ray filter 101, transmission of an infrared ray (the wavelength thereof is 3.3, 4.7, 5.3 or 6.2 $\mu$m) is prevented between the outer portion of the gas sensor and the infrared ray detecting body 5 of the inner portion of the gas sensor. On the other hand, if and when the above described infrared ray non-transmitting portions 27, 27 are overlapped with the first infrared ray non-transmitting portions 25, 25, infrared rays to be transmitted between the outer portion of the gas sensor and the infrared ray detecting body 5 in the inner portion of the gas sensor are canceled in the P portion of the narrow band infrared ray filter 101. This state is substantially the same as that in case where the transmission of the infrared ray is prevented. Similarly, in the areas of the first and second infrared ray non-transmitting portions 25, 25 and 27, 27, a transmission of infrared ray is also prevented between the outer portion of the gas sensor and the infrared ray detecting body 5 in the inner portion of the gas sensor. As a result, the amount of incident infrared rays does not change even if the incident infrared rays are intermitted. On the other hand, since, if and when the gas leakage is caused and the gas is filled around the gas sensor, the infrared ray having an absorption wavelength of the gas to be detected are almost absorbed, the amount of incident infrared rays decreases when the second infrared ray non-transmitting portions 27, 27 are overlapped with the first infrared ray non-transmitting portions 25, 25. If and when the first infrared ray non-transmitting portions 25, 25 are overlapped with P portion of the narrow band infrared ray filter 101, the amount of infrared rays incident upon the infrared ray detecting body 5 becomes the same as that in case where the gas leakage is not caused. Accordingly, during gas leakage, the amount of infrared rays incident upon the infrared ray detecting body 5 periodically changes as the second infrared ray non-transmitting portions 27, 27 periodically move and thus the detection of gas leakage can be continuously made. Furthermore, since the amount of incident infrared rays sharply and largely changes, a detection signal outputted in a lead terminal 17 is sufficiently large and thus the signal-noise ratio is extremely excellent.

Figure 23:
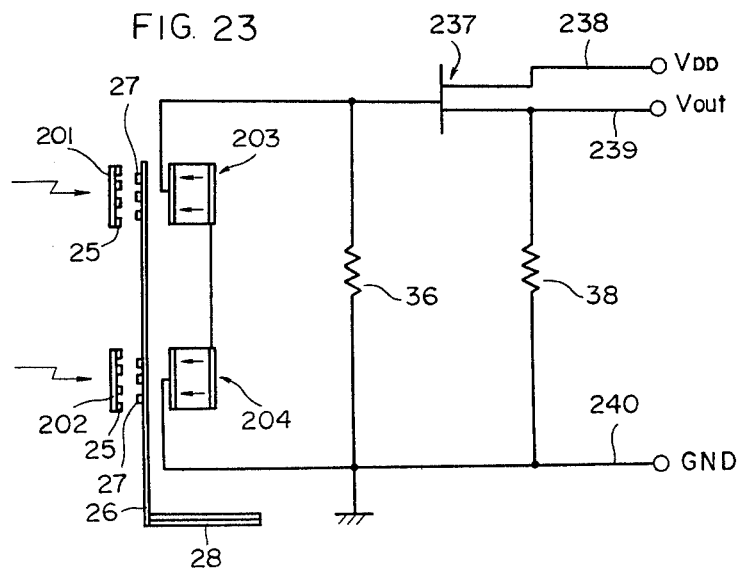
FIG. 23 is a circuit of an infrared ray detector of the ninth embodiment of the present invention as shown in FIG. 22.
Figure 22:
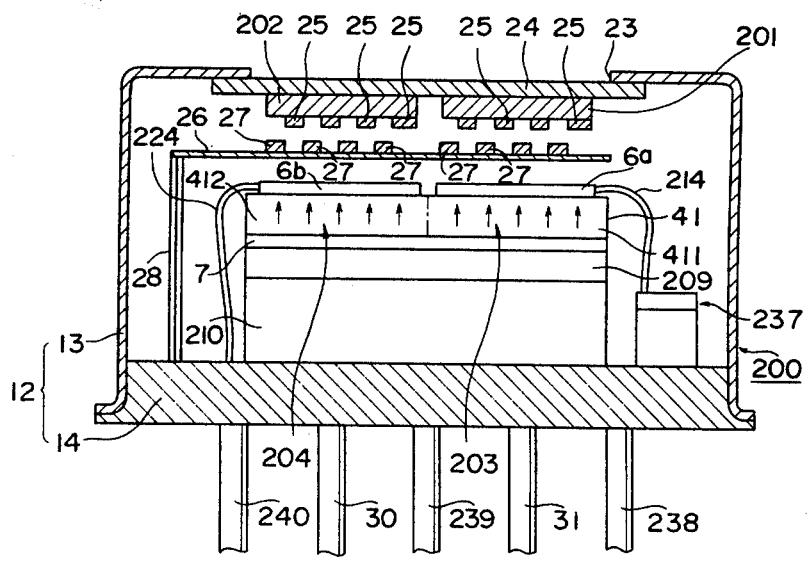
FIG. 22 is a side sectional view of an infrared ray detector of the ninth embodiment of the present invention, wherein an infrared ray detecting body comprises a plurality of infrared ray detecting portions and a plurality of narrow-band filters are disposed opposing to each of the infrared ray detecting portions.

FIG. 22 is a side sectional view of the ninth embodiment of the present invention and FIG. 23 is a circuit of the embodiment as shown in FIG. 22.

The feature of the FIG. 22 embodiment resides in the point that two narrow band infrared ray filters 201 and 202 are sticked to a lower surface of the first infrared ray transmitting portions 24 and the first infrared ray non-transmitting portion 25 is provided in a lower surface of these filters 201 and 202. On the other hand, the second infrared ray non-transmitting portions 27, 27 are provided on the second infrared ray transmitting portion opposed to the first infrared ray non-transmitting portions 25. One opposing portion comprises the first infrared ray non-transmitting portions 25, 25 and infrared ray transmitting spaces between the first infrared ray non-transmitting portions 25, 25, and the other opposing portion comprises the second infrared ray non-transmitting portions 27, 27 and infrared ray transmitting spaces between the second infrared ray non-transmitting portions 27, 27. The other features of the embodiment resides in the fact that two infrared ray detecting portions 203 and 204 are provided opposing to two filters 201 and 202 and that adhesive 209 is made of insulating adhesive such as epoxy resin. The other structures are the same as the first embodiment of the present invention as shown in FIG. 2 and thus the same reference numerals as used in FIG. 2 are also labeled in FIG. 22 so that the detailed description will be omitted.

Two narrow band filters 201 and 202 are filters for human body detection and for fire prevention and the transmission wavelengths thereof are different from each other. More particularly, the filter 202 for fire detection is a bandpass filter which selectively transmits infrared rays having a wavelength in the range of 0.8-7 $\mu$m and substantially cuts infrared rays having wavelengths out of the range. On the other hand, the filter 201 for human body detection is a low cut (high-pass) filter which selectively transmits infrared rays having a wavelength over 5 $\mu$m and substantially cuts infrared rays having a wavelength shorter than 5 $\mu$m. Such structure of two filters 201 and 202 can securely make both of human body detection and fire detection.

The infrared ray detecting portions 203 and 204 are structured such that two electrodes 6a and 6b are provided by dividing into two portions a surface electrode 6 on an upper surface of the infrared ray detecting body 5 comprised of a pyroelectric substrate such as lithium tantalate ($LiTaO_3$). The back surface electrode 7 is commonly used.

The front surface electrodes 6a and 6b in the detecting portions 203 and 204 are connected to one ends of the lead lines 214, 224, respectively, of gold line and the like. A junction type of field effect transistor 237 is provided on the header 14, the other end of lead line 214 being connected to the gate electrode of the field effect transistor 237. The FET 237 corresponds to the impedance converter circuit 11 of FIG. 2. Other end of the lead line 224 is connected to the header 14. The drain and source of the FET 237 are connected to the lead terminals 238 and 239 insulated from the header 14 and another lead terminal 240 is rendered the same voltage as the header 14. These lead terminals are used for connecting to external circuit.

A bimorph vibrator 28 using piezoelectric plates is uprightly provided on the header 14 so that the plate 28 is perpendicular to the header 14. Other structures are the same as the first embodiment of the present invention as shown in FIG. 2 and thus the detailed description will be omitted.

FIG. 23 is an electrical circuit of the infrared ray detector 200 of the embodiment as shown in FIG. 22. The header 14 and the lead terminal 240 are set to an earth level and a positive potential $V_{DD}$ is applied to the drain of the FET 237 or the lead terminal 238, so that the output $V_{out}$ can be obtained from the source of the FET or the lead terminal 239. A gate resistor 36 in order of $10^9$ to $10^{11}$ $\Omega$ and a source resistor 38 of approximate 10 k$\Omega$ are connected, respectively, between the gate and source of the FET 237 and the header 14 or lead terminal 240 of the ground level so that self bias is applied. The gate resistor 36 is disposed within the cap 13 together with the FET 237 and the source resistor 38 is of a type connected in the external. In the infrared ray detector of this embodiment, since the detecting portions 203 and 204 share a pyroelectric substrate and the back surface electrode 7 is commonly used, two detecting portions are connected in series so that the direction of polarization opposite to each other.

The infrared ray detector 200 of the ninth embodiment of the present invention as described in the foregoing will operate in the following. If and when infrared rays radiated by a human body enter into the infrared ray detector 200, most of the infrared rays passes through only the filter 201 and thus negative charges are generated on the side of the front surface electrode 6a of the detecting portion 203, which follows that the output $V_{out}$ decreases to a lower level than that in a normal state. If and when a fire is caused and infrared rays are radiated from flame, for example, to enter into the infrared ray detector 200, most of the infrared rays passes through only the filter 202 and thus negative charges are generated on the side of the front surface electrode 6b of the detecting portion 204, which follows that the output $V_{out}$ increases to an upper level than that in a normal state. Such level change in the output $V_{out}$ is utilized in a remote alarm, an alarm and the like depending on circuits connected to the lead terminal 239.

In the infrared ray detector 200, since two detecting portions 203 and 204 are connected in series so that the directions of polarization are opposite to each other and both detecting portions have the same area, a charging effect to an atmosphere temperature within a series circuit is cancelled and thus the change of the FET output hardly arises. Since a pyroelectric element indicates a piezoelectric effect as already known, a piezoelectric effect appears in the detecting portions 203 and 204 if and when a door in the closed room in which the present apparatus is fitted is sharply closed. However, the direction of polarization are opposite to each other, such piezoelectric effect can be cancelled. Meanwhile, the light receiving areas of the two detecting portions 203 and 204 are not necessarily equal to each other and the difference between the light receiving areas can be permissible unless such difference adversely affect an operation of the circuit.

Although, in the infrared ray detector 200, a pyroelectric substrate and back surface electrode 7 are common and two detecting portions 203 and 204 are connected in series so that the polarization direction of the two portions 203 and 204 are opposite to each other, the same meritorious effects are brought about even if the two detecting portions 203 and 204 are structured independently and both are connected in parallel so that the polarization directions are opposite to each other.

Figure 24:
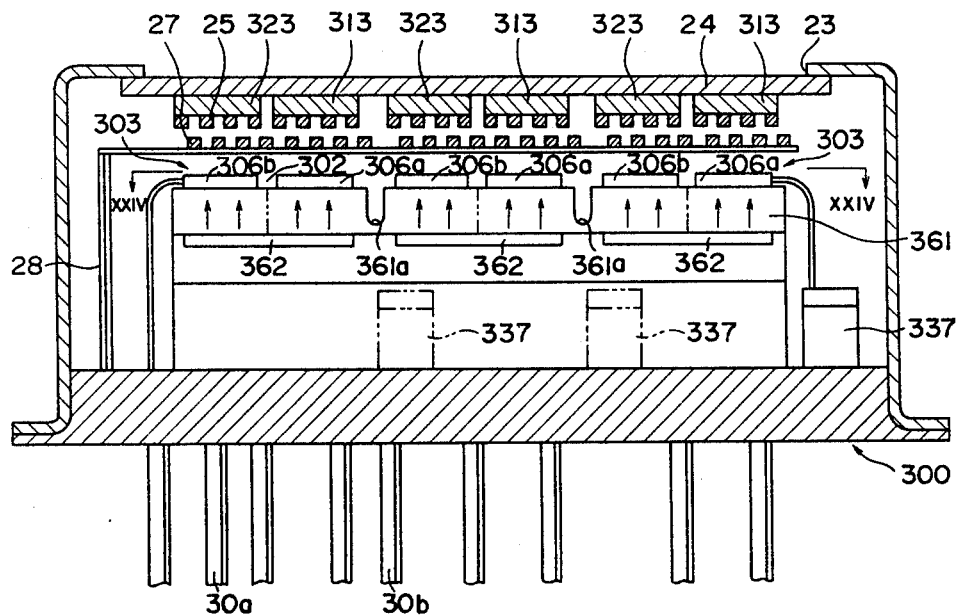
FIG. 24 is a side sectional view of an infrared ray detector of the tenth embodiment of the present invention, wherein a plurality of infrared ray detecting portions are arrayed in a matrix manner.
Figure 25:
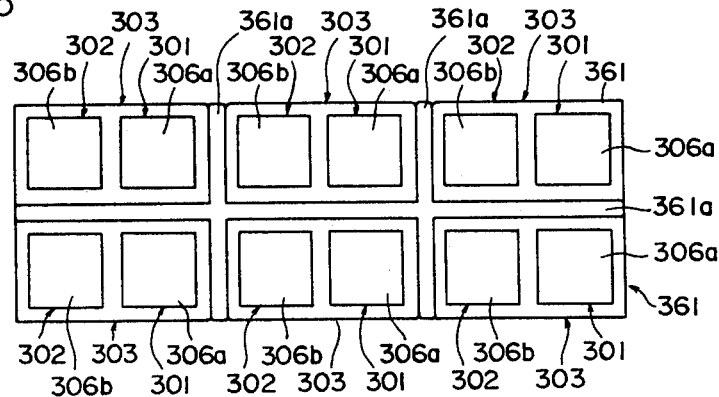
FIG. 25 is a partial plan view along the line XXV—XXV in FIG. 24.

FIG. 24 is a side sectional view showing an infrared ray detector 300 of the tenth embodiment of the present invention and FIG. 25 is a partial plan view along a line XXIV—XXIV in FIG. 24. The features of the present embodiment reside in the fact that a plurality of sets of detecting units 303 are arranged in a matrix manner, each set comprising an element 301 provided for human body detection and an element 302 provided for fire detection. As clearly seen from FIG. 25, two row and six column of square front surface electrode layers 306a and 306b are formed by evaporation on the surface of a rectangular substrate 361, with a predetermined distance. A back surface electrode layer 362 is formed in a back surface of the substrate 361 in such a manner that the layer 362 is matched with the portions opposing to a set of front surface electrode layers 306a and 306b, so that the same number of detecting units 303 has the number of the back surface electrode layers 362, that is, a sixth detecting units 303 are provided. One element 301 comprises a single front surface electrode layer 306a, a portion of the back surface electrode layer 362 opposing to the layer 306a, and a region of a pyroelectric substrate 361 interposed therebetween, and another element 302 comprises a surface electrode layer 306b adjacent to the front surface electrode layer 306a and opposing to the same back face electrode layer 362 as described in the foregoing, the back face electrode layer 362, and a region of the pyroelectric substrate 361 interposed therebetween. A single detecting unit 303 is structured by these two detecting element 301 and 302. A groove 361a is formed in a surface of the pyroelectric substrate 361 in a portion partitioning a respective detecting unit 303, that is, in a position on a front surface side opposing to gap portion in which the back surface electrode layer 362 is not provided. Although the groove 361a is effective in that mutual thermal effect between detecting units 303 is reduced, the groove 361a is not necessarily an indispensable constituent element.

On the other hand, optical filters 313 and 323, the transmission wavelength ranges of which are different from each other, are provided in a lower surface of the infrared ray transmitting portion 24 which closes an opening 23 in the cap 13, the optical filters 313 and 323 being opposed to the front surface electrode layers 306a and 306b of each of detecting elements 301 and 302. Other structures are the same as the ninth embodiment of the present invention as described in the foregoing, that is, the infrared ray detector 200 (as shown in FIG. 22) and thus the detailed description will be omitted.

Since the infrared ray detector 300 as shown in FIG. 24 is structured such that a plurality of detecting units 303 are provided in a matrix manner, the detector 300 can detect a change of output of the source of the FET 337 in each detecting unit 303, and can detect moving direction of human body or moving direction of fire and thus can extremely securely specify the traveling path of a human body or the fire source.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An infrared ray detector comprising:
    an infrared ray detecting body,
    a pair of opposing portions having a plurality of infrared ray non-transmitting portions and infrared ray transmitting portions,
    intermitting means for intermitting infrared rays incident upon said infrared ray detecting body through said pair of opposing portions, said intermitting means comprising a vibrator connected to one of said pair of opposing portions, wherein a state that the infrared ray transmitting portions of both opposing portions are substantially overlapped with respect to each other and the infrared ray non-transmitting portions of both opposing portions are substantially overlapped with respect to each other, and a state that the infrared ray non-transmitting portions and transmitting portions of one opposing portion are substantially overlapped with the infrared ray transmitting portions and non-transmitting portions of the other opposing portion, respectively, are alternately repeated, and
    a housing containing said infrared ray detecting body, said pair of opposing portions and said intermitting means, said housing being provided with an opening for incidence of infrared rays.

2. An infrared ray detector in accordance with claim 1, wherein the two dimensional shape of said infrared ray transmitting portions and infrared ray non-transmitting portions are linear.

3. An infrared ray detector in accordance with claim 1, wherein said infrared ray detecting body comprises a pyroelectric type infrared ray detecting body for generating electric charges according to an amount of change of incident infrared rays.

4. An infrared ray detector in accordance with claim 1, which further comprises an infrared ray transmitting filter closing said opening.

5. An infrared ray detector in accordance with claim 1, which further comprises
an impedance converter circuit connected to said infrared ray detecting body, said impedance converter circuit converting an output impedance of the infrared ray detecting body into a low resistance, and being contained within said housing.

6. An infrared ray detector in accordance with claim 5, which further comprises
a shield element for shielding said infrared ray detecting body and said impedance converter circuit from an electrical noise due to said vibrator.

7. An infrared ray detector in accordance with claim 6, wherein said shield element is provided with an incident port of infrared rays, the other of said pair of opposing portions being sticked to said incident port of infrared rays.

8. An infrared ray detector in accordance with claim 1, which further comprises
a shield element for shielding said infrared ray detecting body from an electrical noise due to said vibrator.

9. An infrared ray detector in accordance with claim 8, wherein said shield element is provided with an incident port of infrared rays, the other of said pair of opposing portions being sticked to said incident port of infrared rays.

10. An infrared ray detector in accordance with claim 1, which further comprises
a filter closing said opening and being mounted in the vicinity of said opening, and wherein
the other of said pair of opposing portions is sticked to the inner surface side of said filter.

11. An infrared ray detector in accordance with claim 1, wherein said vibrator is disposed such that the longitudinal direction thereof is coincident with an incident direction of infrared ray.

12. An infrared ray detector in accordance with claim 1, wherein one of said pair of opposing portions is disposed so as to vibrate in a direction parallel to the other opposing portion.

13. An infrared ray detector in accordance with claim 12, wherein said vibrator is disposed such that the longitudinal direction thereof is coincident with a direction perpendicular to said incident direction of infrared rays.

14. An infrared ray detector in accordance with claim 1, wherein said infrared ray transmitting portions and infrared ray non-transmitting portions of said pair of opposing portions are shaped such that the infrared ray transmitting portions in one opposing portion are completely overlapped with the infrared ray non-transmitting portions in the other opposing portion when shutting off the infrared rays and the infrared ray transmitting portions in one opposing portion are completely overlapped with the infrared ray transmitting portions in the other opposing portion when transmitting the infrared rays.

15. An infrared ray detector in accordance with claim 14, wherein
said pair of opposing portions are structured such that the shape and size of the infrared ray transmitting portions and infrared ray non-transmitting portions of one opposing portion are the same with respect to each other and the lengths in directions of vibration of the infrared ray transmitting portions are respectively 1/n of amounts of displacement based on vibration of the respective portion, wherein n is an integer, and the shape and size of the infrared ray transmitting portions and infrared ray non-transmitting portions in the other opposing portion are the same as those of the infrared ray transmitting portions and the infrared ray non-transmitting portions in said one opposing portion.

16. An infrared ray detector in accordance with claim 1, wherein said vibrator comprises a piezoelectric vibrator.

17. An infrared ray detector in accordance with claim 1, which further comprises
infrared ray transmitting filter opposed to said opening,
said infrared ray transmitting filter being a narrow band infrared ray filter for substantially transmitting only an infrared ray absorbed by the gas to be detected.

18. An infrared ray detector in accordance with claim 1, which further comprises
a plurality of infrared ray filters opposed to said opening, and wherein
said infrared ray detecting body comprises a plurality of detecting portions,
a plurality of said filters being provided opposing to each of said detecting portions and having inherent transmitting band.

19. An infrared ray detector in accordance with claim 18, wherein said plurality of filters comprise filters transmitting an infrared ray radiated from fire for fire prevention and filters transmitting an infrared ray radiated from human body for human body detection.

20. An infrared ray detector in accordance with claim 18, wherein said plurality of detecting portions are connected in such a manner that directions of polarization for each pair are opposite to each other.

21. An infrared ray detector in accordance with claim 18, wherein said plurality of detecting portions are arrayed in a matrix manner.

22. An infrared ray detector comprising:
an infrared ray detecting body,
a pair of opposing portions having a plurality of infrared ray non-transmitting portions and infrared ray transmitting portions,
intermitting means for intermitting infrared rays incident upon said infrared ray detecting body through said pair of opposing portions, said intermitting means comprising a pair of vibrators connected to said pair of opposing portions, respectively, wherein a state that the infrared ray transmitting portions of both opposing portions are substantially overlapped with respect to each other and the infrared ray non-transmitting portions of both opposing portions are substantially overlapped with respect to each other, and a state that the infrared ray non-transmitting portions and transmitting portions of one opposing portion are substantially overlapped with the infrared ray transmitting portions and non-transmitting portions of the other opposing portion, respectively, are alternately repeated, and a housing containing said infrared ray detecting body, said pair of opposing portions and said intermitting means, said housing being provided with an opening for incidence of infrared rays.

23. An infrared ray detector in accordance with claim 22, which further comprises an impedance converter circuit connected to said infrared ray detecting body, said impedance converter circuit converting an output impedance of the infrared ray detecting body into a low resistance, and being contained within said housing.

24. An infrared ray detector in accordance with claim 22, which further comprises a shield element for shielding said infrared ray detecting body from an electrical noise due to said vibrator.

25. An infrared ray detector in accordance with claim 22, wherein said pair of vibrators are disposed so that the longitudinal direction thereof is coincident with an incident direction of infrared rays.

26. An infrared ray detector in accordance with claim 22, wherein said pair of vibrators are disposed so that the longitudinal direction thereof is coincident with a direction perpendicular to an incident direction of infrared rays.

27. An infrared ray detector in accordance with claim 22, wherein said pair of vibrators comprise piezoelectric vibrators.

28. An infrared ray detector in accordance with claim 22, which further comprises a plurality of infrared ray filters opposed to said opening, and wherein said infrared ray detecting body comprises a plurality of detecting portions, and a plurality of said filters are provided opposing to each of said detecting portions and having inherent transmitting band.

29. An infrared ray detector in accordance with claim 28, wherein said plurality of filters comprise filters transmitting an infrared ray radiated from fire for fire prevention and filters transmitting an infrared ray radiated from human body for human body detection.

30. An infrared ray detector in accordance with claim 28, wherein said plurality of detecting portions are connected in such a manner that directions of polarization for each pair are opposite to each other.

31. An infrared ray detector in accordance with claim 28, wherein said plurality of detecting portions are arrayed in a matrix manner.

32. An infrared ray detector in accordance with claim 22, wherein said infrared ray detecting body comprises a pyroelectric type infrared ray detecting body for generating electric charges according to an amount of change of incident infrared rays.

33. An infrared ray detector in accordance with claim 22, which further comprises an infrared ray transmitting filter closing said opening.

34. An infrared ray detector in accordance with claim 33, wherein said pair of opposing portions are structured such that the shape and size of the infrared ray transmitting portions and infrared ray non-transmitting portions of one opposing portion are the same with respect to each other and the lengths in directions of vibration of the infrared ray transmitting portions are respectively 1/n of amounts of displacement bases on vibration of the respective portion, wherein n is an integer, and the shape and size of the infrared ray transmitting portions and infrared ray non-transmitting portions in the other opposing portion are the same as those of the infrared ray transmitting portions and the infrared ray non-transmitting portions in said one opposing portion.

35. An infrared ray detector in accordance with claim 22, wherein said infrared ray transmitting portions and infrared ray non-transmitting portions of said pair of opposing portions are shaped such that the infrared ray transmitting portions in one opposing portion are completely overlapped with the infrared ray non-transmitting portions in the other opposing portion when shutting off the infrared rays and the infrared ray transmitting portions in one opposing portion are completely overlapped with the infrared ray transmitting portions in the other opposing portion when transmitting the infrared rays.

36. An infrared ray detector in accordance with claim 35, which further comprises an impedance converter circuit connected with said infrared ray detecting body, the impedance converter circuit converting an output impedance of the infrared ray detecting body into a low resistance, and being continued with said housing, and a shield element for shielding said infrared ray detecting body and said impedance converter circuit from an electrical noise due to said vibrator.

37. An infrared ray detector in accordance with claim 22, which further comprises infrared ray transmitting filter opposed to said opening, said infrared ray transmitting filter being a narrow band infrared ray filter for substantially transmitting only an infrared ray absorbed by the gas to be detected.

* * * * *